(12) United States Patent
Babcock

(10) Patent No.: US 8,426,008 B2
(45) Date of Patent: *Apr. 23, 2013

(54) GRADIENT COATINGS WITH BIOPOLYMER-RESISTANT DOMAINS

(75) Inventor: Brian David Babcock, Bloomington, MN (US)

(73) Assignee: Brian Babcock, Bloomington, MN (US)

( * ) Notice: Subject to any disclaimer, the term of this patent is extended or adjusted under 35 U.S.C. 154(b) by 12 days.

This patent is subject to a terminal disclaimer.

(21) Appl. No.: 13/326,321

(22) Filed: Dec. 15, 2011

(65) Prior Publication Data

US 2012/0082826 A1    Apr. 5, 2012

Related U.S. Application Data

(63) Continuation of application No. 12/803,576, filed on Jun. 30, 2010, now Pat. No. 8,101,263, which is a continuation of application No. 10/494,122, filed as application No. PCT/US02/35134 on Nov. 1, 2002, now Pat. No. 7,790, 265.

(60) Provisional application No. 60/335,165, filed on Nov. 1, 2001.

(51) Int. Cl.
    *B32B 5/14*    (2006.01)

(52) U.S. Cl.
    USPC .......... 428/141; 428/144; 428/145; 428/147; 428/148; 428/409; 428/410; 428/156; 428/164; 977/858; 977/857; 977/962

(58) Field of Classification Search .................. 428/141, 428/145, 147, 148, 409, 410, 156, 164, 144; 997/858, 857, 962

See application file for complete search history.

(56) References Cited

U.S. PATENT DOCUMENTS

| 5,512,131 | A  | * | 4/1996 | Kumar et al. | ................. 438/738 |
| 6,235,340 | B1 | * | 5/2001 | Lee et al. | ..................... 427/2.12 |
| 6,770,323 | B2 | * | 8/2004 | Genzer et al. | .............. 427/248.1 |
| 7,790,265 | B2 | * | 9/2010 | Babcock | ....................... 428/141 |
| 8,101,263 | B2 | * | 1/2012 | Babcock | ....................... 428/141 |

\* cited by examiner

*Primary Examiner* — William P Watkins, III

(74) *Attorney, Agent, or Firm* — Babcock Legal Services

(57) ABSTRACT

A medical device or analytical device comprising a fluid-impervious surface comprising a base surface, at least one distinct region of the base surface covered by a mixed monolayer film, the mixed monolayer film comprising a species having a functional group M1 and a species having a functional group M2 where M1 and M2 have different surface energies, the mixed monolayer forming a surface energy gradient wherein at least one of the species used to form the monolayer on the surface comprises a biopolymer-resistant domain.

18 Claims, 9 Drawing Sheets

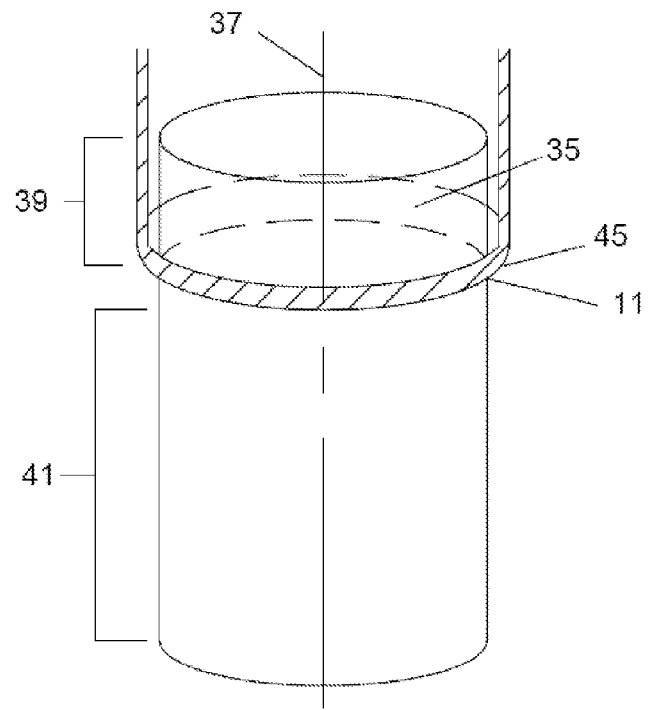
FIG. 9
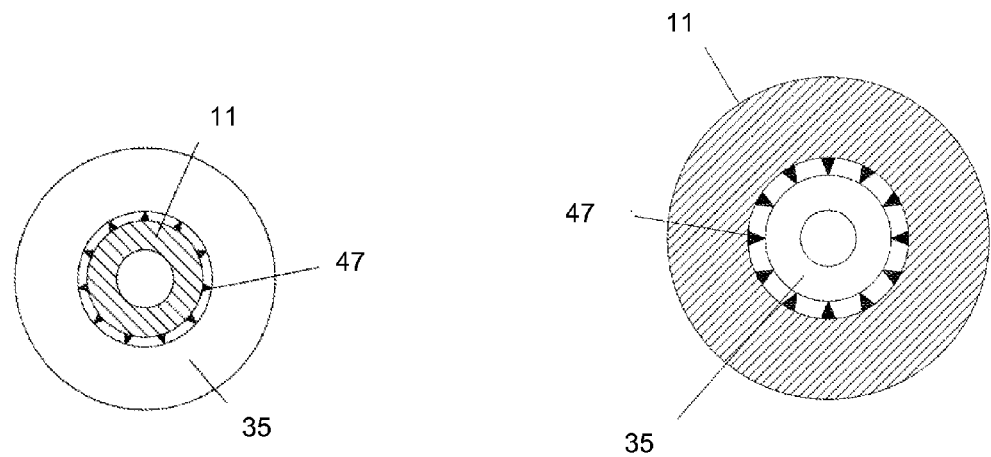
FIG. 10  FIG. 11

GRADIENT COATINGS WITH BIOPOLYMER-RESISTANT DOMAINS

CROSS-REFERENCES TO RELATED APPLICATIONS

This application is a continuation of and claims the benefit of U.S. application Ser. No. 12/803,576 filed Jun. 30, 2010 which is a continuation of U.S. application Ser. No. 10/494,122 filed Aug. 12, 2004 (now U.S. Pat. No. 7,790,265) which is the National Phase of PCT Application PCT/US02/35134 filed Nov. 1, 2002 which claims priority to provisional application 60/335,165 filed Nov. 1, 2001, the contents of Ser. No. 10/494,122 is herein incorporated by reference in its entirety.

STATEMENT REGARDING FEDERALLY SPONSORED RESEARCH OR DEVELOPMENT

Not Applicable.

PARTIES TO A JOINT RESEARCH AGREEMENT

Not Applicable.

FIELD OF THE INVENTION

This invention relates to a surface-energy gradient on a fluid-impervious surface and method of its creation.

BACKGROUND OF THE INVENTION

Microscopic fluidic devices, ranging from surgical endoscopes and microelectromechanical systems to the commercial 'lab-on-a-chip', allow chemical analysis and synthesis on scales unimaginable a few decades ago (Kataoka and Troian, 1999). Advances in micro fabrication techniques have led to the ability to manufacture flow channels ranging from a few hundred angstroms to a few hundred microns (Pfahler, et al, 1990). However, due to the microscopic scale of the systems involved, fluid transport and friction losses are problematic. Different methods using temperature, pressure, or electric potential gradients have been developed to transport fluid through these systems. Each of these methods increases the energy required to operate such systems, and none of the methods solve the problem of fluid friction losses.

Friction arises from the adhesive forces between two surfaces in contact In the absence of wear and plastic deformation, as is the case in fluid transport in microscale systems, friction is largely attributable to interfacial effects (Krim, 1996). For laminar flow in channels, fluid friction loss (f) can be estimated as $f = 16/Re$ where $Re$ = Reynolds Number ($\rho \, v \, D_C / \mu$)
$\rho$ = density of fluid
$v$ = fluid velocity
$D_c$ = effective diameter of channel
$\mu$ = viscosity of fluid Therefore, as Dc begins to approach micron and angstrom dimensions, friction loss increases greatly.

Organic thin films have been used to control friction and wear in a variety of machines. As machines get even smaller, and lubricating films approach the monolayer regime, self-assembled monolayer films show great potential for use in such items. SAM films have been shown to reduce the friction between two surfaces. By changing the energy of the surface, the SAM can prevent a fluid such as water from wetting the surface. A reduction in the attraction between the fluid and the tail group of the SAM will result in a reduction in friction.

Several studies have been conducted on the frictional properties of SAMs. These studies have shown how friction varies depending on the structure and composition of the SAM. Most of these studies used Atomic Force Microscopy (AFM) to measure friction. This measurement is performed by passing the AFM probe tip over the SAM surface. The frictional response of the surface is measured by the AFM as the normal force exerted by the probe is varied. In their 1996 paper, Xiao et al determined how the chain length of the SAM affected friction. Their work with mica surfaces showed that longer-chain SAMs reduce friction the most. Longer chain molecules form films that are typically more densely packed and more crystalline in structure than shorter chain molecules do. The enhanced crystalline structure and better packing provide a lower friction surface (Liu and Evans, 1996). Their work with SAM films on gold surfaces led to the same conclusions regarding chain length and crystalline structure.

The effect of the tail group was then studied. Researchers determined that frictional behavior closely followed the variation of the adhesive properties, meaning low-energy surfaces had the lowest friction while high-energy surfaces such as —NH2 produced higher amounts of friction loss (Tsukruk and Bliznyuk, 1998). Kim et al in 1999 found that among low energy surfaces, those with the smallest head group yielded the surface with the lowest friction. Specifically, CF3-terminated films had three times the friction of CH3-terminated films.

In addition to lowering the friction between two surfaces, SAMs can have a dramatic effect on the ability of a fluid to wet a surface. For instance, CH3-terminated SAMs produce low energy, hydrophobic surfaces that are not wet by water while CO2H-terminated SAMs produce high energy, hydrophilic surfaces that are almost completely wet by water. The contact angle that water forms with a surface is a good indication of the surface's hydrophilicity or hydrophobicity. For instance, water forms a contact angle of 115° with CH3 surfaces while it forms a contact angle of <15° with CO 2H surfaces. In general, as the contact angle decreases, water has more affinity for the surface and will more easily wet it (Laibinis et al, 1998).

A system that reduced friction losses and improved fluid transport would have a great benefit.

All US patents and applications and all other published documents mentioned anywhere in this application are incorporated herein by reference in their entirety.

Without limiting the scope of the invention a summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

SUMMARY OF THE INVENTION

The proposed system uses self-assembled monolayer (SAM) films to modify a surface; a novel design is proposed which modifies the surface using a mixed SAM surface so that fluids are transported with minimal or reduced external forces required. The proposed design will result in microfabricated systems that are smaller and more energy-efficient.

In one embodiment a method of derivatizing a fluid-impervious surface with a mixed monolayer to create a surface energy gradient comprises the following steps:

a) exposing a base surface having a proximal and a distal portion to a first solution comprising a plurality of molecules of the formula X1-J1-M1, wherein X1 and M1 represent separate functional groups and J1 represents a spacer moiety that, together, are able to promote formation from solution of a self-assembled monolayer for sufficient time to form a monolayer surface having a substantially uniform surface energy on the base surface, b) removing a portion of the monolayer of step (a) such that a portion of the base surface is again fully or partially exposed, c) exposing the portion of the base surface from (b) to a second solution comprising a plurality of molecules of the formula X2-J2-M2 and a plurality of molecules of the formula X1-J1-M1 wherein the functional group M2 has a different surface energy from that of the functional group M1 such that a surface energy gradient from a proximal location to a distal location is formed.

In another embodiment, removing a portion of the monolayer is done while the base surface and monolayer surface are immersed in either the first solution or the second solution.

In another embodiment removal of a portion of the monolayer of (a) is performed using a method or combination of methods selected from the group consisting of 1) passing an instrument along the monolayer surface created in (a) with sufficient force to remove a portion of the monolayer created in (a), 2) etching chemically the portion to be removed, 3) etching physically the portion to be removed, 4) cutting with a laser, 5) cutting with water, 6) etching through thermometric exposure, 7) removing with grit, 8) drilling, 9) sonic means, and 10) cutting with an instrument.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there are further embodiments of the invention illustrated and described.

BRIEF DESCRIPTION OF THE DRAWINGS

FIG. 9 illustrates a side elevational schematic view of a method for creating a gradient along the outside walls of the tube.

FIG. 10 illustrates a cross-sectional schematic view of the tube and instrument in which the instrument has at least one tip used in the method for creating a surface energy gradient on the interior of the tube.

FIG. 11 illustrates a cross-sectional schematic view of the tube and instrument in which the instrument has at least one tip used in the method for creating a surface energy gradient on the outside of the tube.

DETAILED DESCRIPTION OF THE INVENTION

Figure 1A:
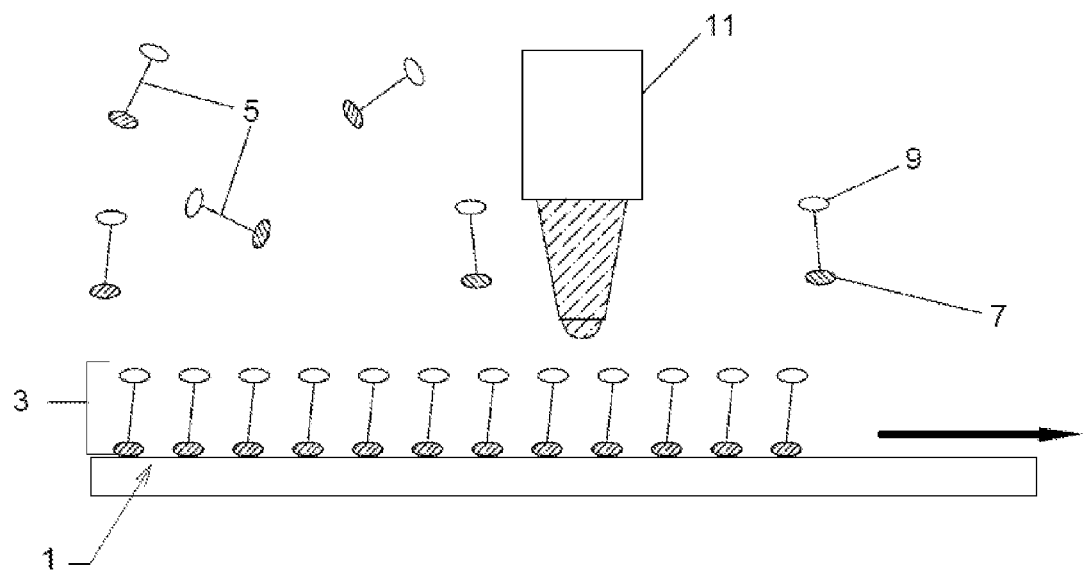
FIG. 1 illustrates a blown-up schematic view of the method for producing a mixed monolayer surface energy gradient.
Figure 1B:
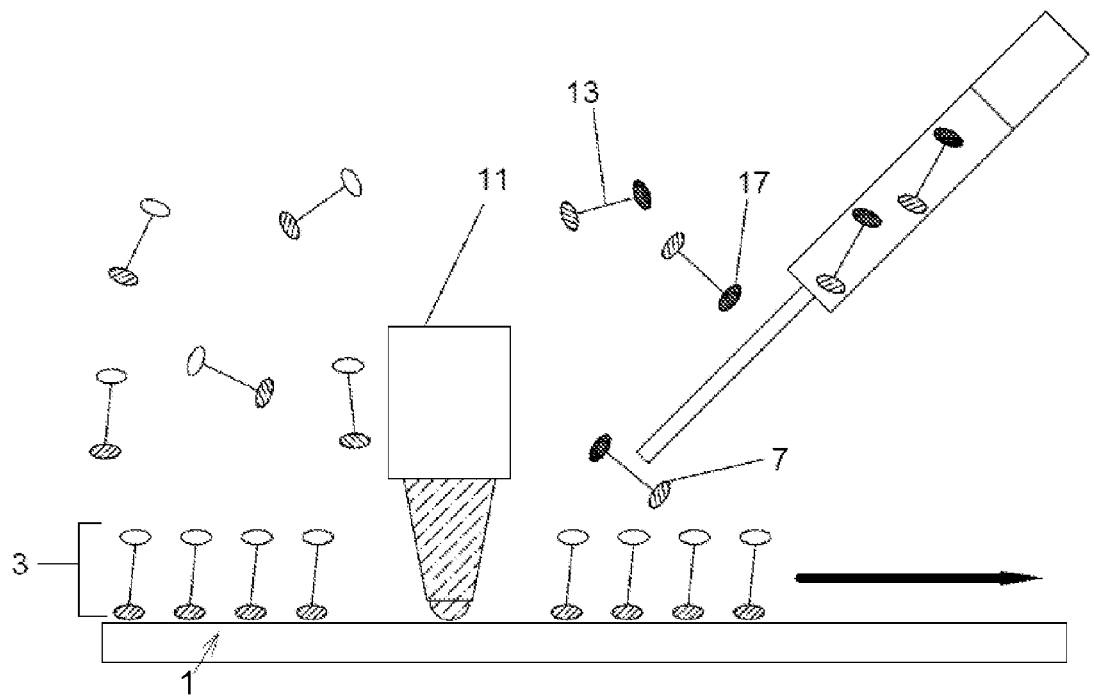
Figure 1C:
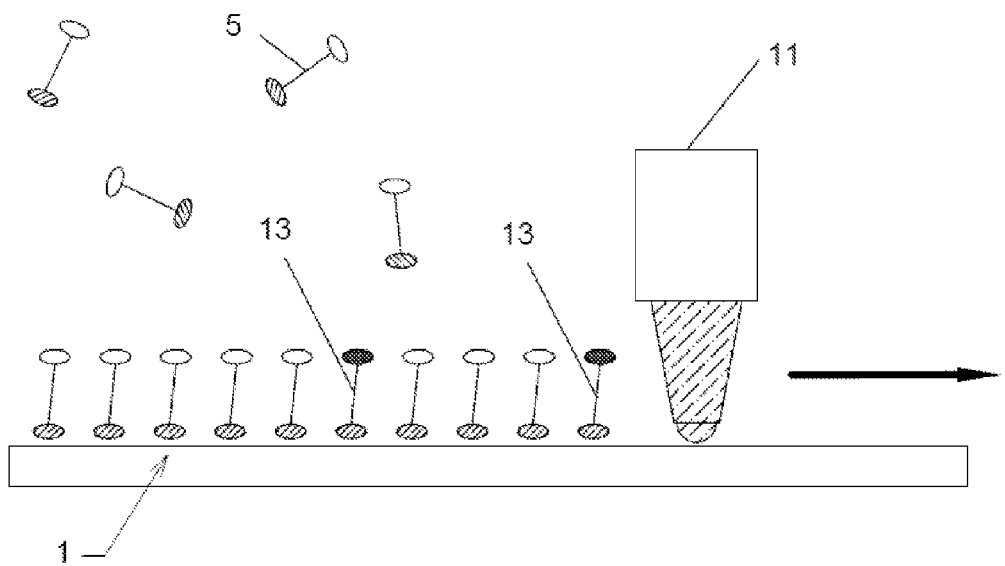
Figure 1D:
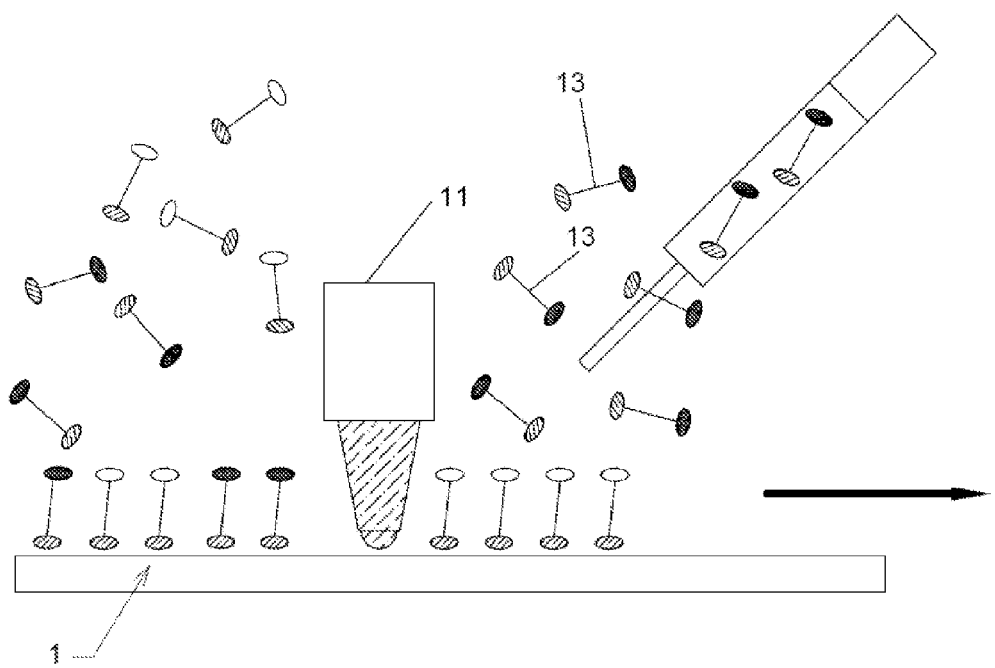
Figure 1E:
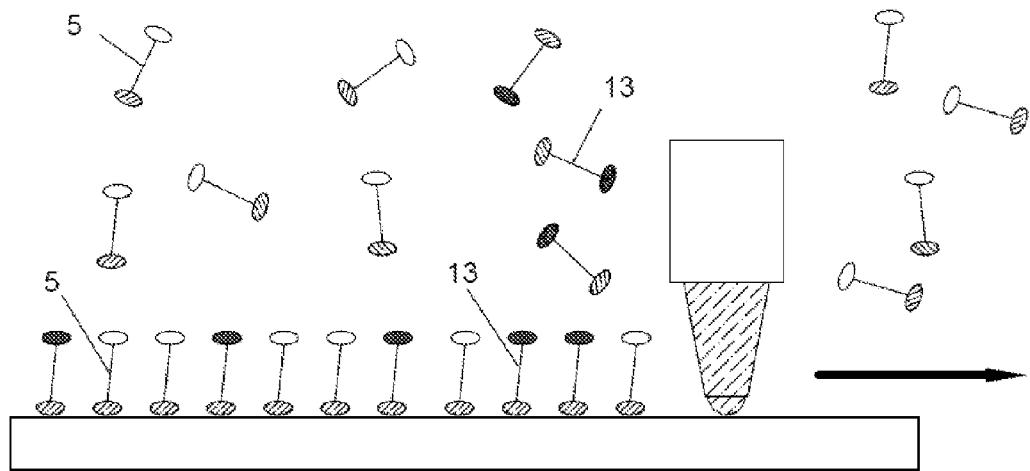
Figure 1F:
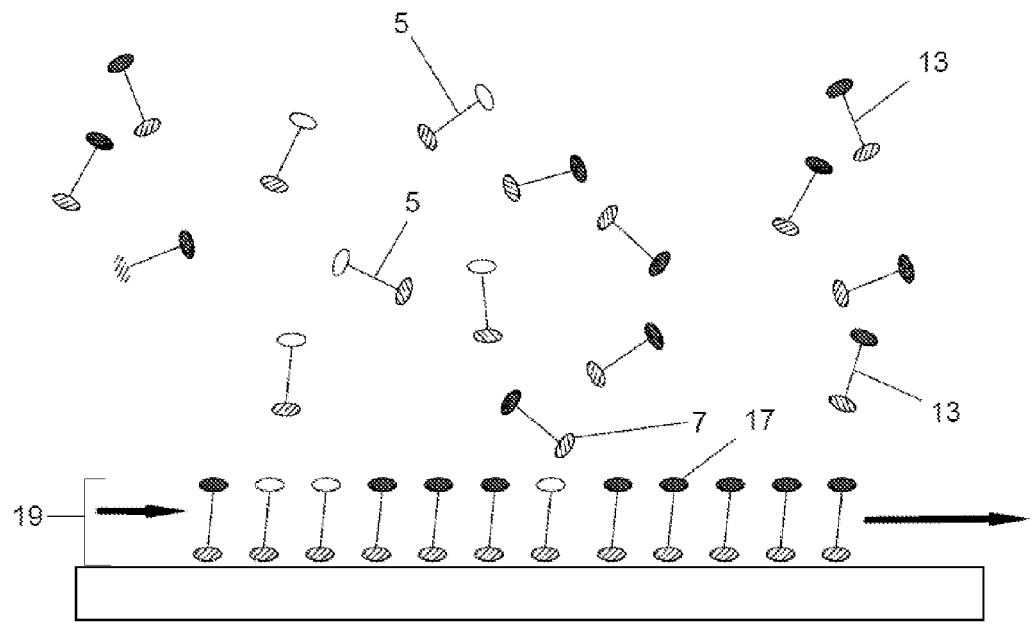

While this invention may be embodied in many different forms, there are described in detail herein specific preferred embodiments of the invention. This description is an exemplification of the principles of the invention and is not intended to limit the invention to the particular embodiments illustrated.

As used herein, the term "tube" is any hollow object open on two sides without limitation by cross-sectional geometries.

Turning now to the drawings, FIG. 1 shows a blown-up schematic view of an embodiment of the method for producing a mixed monolayer surface energy gradient. The view consists of 6 slides. Slide (a) shows a base surface 1 having a monolayer 3. The original monolayer is made up of a plurality of first organic molecules 5. The base surface 1 having a monolayer 3 can be stored and used later as well. The first organic molecules 5 are comprised of a functional group 7 (e.g. thiol) that reacts with the base surface 1 and a low surface energy functional group 9 (e.g. $CH_3$, $CF_3$, etc). The instrument 11 is not in contact with the monolayer 3 at this point of the process. The instrument 11 in slide (b) comes into contact with the monolayer 3 and removes some of the original monolayer 3 as the instrument 11 passes along the surface 1. At the same time, second organic molecules 13 are added. The second organic molecules 13 are comprised of a functional group 7 designed to react with the base surface 1 and a high surface energy functional group 17 (e.g. OH, $CO_2H$, $CONH_2$, etc). Slide (c) shows how some of the second organic molecules 13 are reacting with the base surface 1 and creating a mixed SAM layer. As shown in slide (d), this process continues as the instrument 11 continues along the base surface 1. More second organic molecules 13 are being added and are reacting with the exposed base surface 1. This continues through slide (e) and in slide (f) a higher concentration of high energy groups 17 make up the monolayer 3 and along the portion of the surface the instrument 11 passed, a surface energy gradient 19 is formed.

Unlike prior art examples, the surface energy gradient of this invention is designed to be formed with well-defined dimensions that correspond to the features of the instrument used in the process. The length (L) of the gradient will correspond to the length of the path traced by the instrument while the width (W) of the gradient will correspond to the width or radius of the instrument tip used to expose the base layer. Thus, a very long and thin gradient region can be created with this method with aspect ratios (length divided by width, L/W) that can vary from 2.0, 10.0, to essentially an infinite number. Nanografting using an Atomic Force Microscope (AFM) as the instrument will produce surface energy gradients with very small width dimensions. As an example, AFM instruments with a tip radius of 20-nm could be used in the invention (Liu and Evans, p. 1236, col. 2). Using this instrument, a surface energy gradient region of 20 nm wide by 1000 nm long could be created; such a region would have an aspect ratio of 50. Gradients with higher aspect ratios (10,000 or greater) can be created by increasing the path length traced by the instrument. High aspect ratio gradient regions could also be made using AFMs with tip radii in the 40-500 nm to produce gradient regions with a larger width W (Tsukruk and Bliznyuk, p. 448, col. 1). Other instruments such as those commonly used in micromachining applications can be used. Micromachining applications are capable of using manufacturing channels with widths in the 100-1000 micron range while standard machining techniques can produce channels with widths in the 1.0-10.0-mm range.

In one embodiment a method of derivatizing a fluid-impervious surface with a mixed monolayer to create a surface energy gradient comprises the following steps:
a) exposing a base surface having a proximal and a distal portion to a first solution comprising a plurality of molecules of the formula X1-J1-M1, wherein X1 and M1 represent separate functional groups and J1 represents a spacer moiety that, together, are able to promote formation from solution of a self-assembled monolayer for sufficient time to form a monolayer surface having a substantially uniform surface energy on the base surface,
b) removing a portion of the monolayer of step (a) such that a portion of the base surface is again fully or partially exposed,
c) exposing the portion of the base surface from (b) to a second solution comprising a plurality of molecules of the formula X2-J2-M2 and a plurality of molecules of the formula X1-J1-M1 wherein the functional group M2 has a different surface energy from that of the functional group M1 such that a surface energy gradient from a proximal location to a distal location is formed. The X2 and J2 groups for the molecule in the second solution can be the same as the X1 and J1 groups for the molecule in the first solution, or they can be different, depending on the desired final properties of the mixed monolayer.

In another embodiment, removing a portion of the monolayer is done while the base surface and monolayer surface are immersed in either the first solution or the second solution.

In another embodiment removal of a portion of the monolayer of (a) is performed using a method or combination of methods selected from the group consisting of 1) passing an instrument along the monolayer surface created in (a) with sufficient force to remove a portion of the monolayer created in (a), 2) etching chemically the portion to be removed, 3) etching physically the portion to be removed, 4) cutting with a laser, 5) cutting with water, 6) etching through thermometric exposure, 7) removing with grit, 8) drilling, 9) sonic means, and 10) cutting with an instrument.

In another embodiment, removal of the portion of the monolayer of (a) is performed while at the same time increasing amounts of a third solution comprising a molecule of the formula X2-J2-M2 so that a mixed monolayer surface of M1 and M2 moieties is formed with a molar ratio of M2 to M1 that increases from a proximal location to a distal location of the surface. The X2 and J2 groups for the molecule in the third solution can be the same as the X1 and J1 groups for the molecule in the first solution, or they can be different, depending on the desired final properties of the mixed monolayer In another embodiment, the third solution has a solvent different from that of the first solution or the second solution.

In other embodiments, multiple n solutions comprising molecules of Xn-Jn-Mn can be used to create multiple gradients of mixed monolayers.

In several other embodiments, the gradient is created on 1) the inside of a tube, 2) the outside of a tube, 3) on a rectangular channel having three walls and one side open, 4) on only 1 face of the channel, 5) on 2 faces of the channel, and 6) on 3 faces of the channel.

In another embodiment, the base surface is a metal oxide comprising a metal oxide from the group comprising silica, alumina, quartz, glass, or the like. In some embodiments using metal oxide base surfaces, the functional group X is a carboxylic acid.

In an additional embodiment, the base surface is a metal selected from the group comprising gold, silver, copper, aluminum, cadmium, zinc, palladium, platinum, mercury, lead, iron, chromium, manganese, tungsten, and any alloys of the above. In some embodiments using metals for the base surfaces, the functional group X is a sulfur-containing functional group (e.g. thiols, sulfides, disulfides, and the like). In other embodiments, the metal of the base surface is in the form of a metalized film coating a polymer surface.

In another embodiment, the base surface is doped or undoped silicon. In some embodiments using doped or undoped silicon for the base surface, the functional group X is selected from the group comprising silanes or chlorosilanes.

In another embodiment, the base surface is a metal selected from the group comprising palladium and platinum. In some embodiments using these metals for the base surface, the functional group X is a functional group selected from the group comprising nitrites and isonitriles.

In another embodiment, the base surface is copper. In some embodiments using copper for the base surface, the functional group X is a hydroxamic acid.

In another embodiment, the base surface is gold. In some embodiments using gold for the base surface, the functional group X is at least one sulfur-containing functional group selected from the group consisting of thiols, sulfides, or disulfides.

In another embodiment, the functional group M1, M2, . . . Mn is selected from the group comprising ionic, nonionic, polar, nonpolar, halogenated, alkyl, aryl or other functionalities, In other embodiments, the functional group M1, M2, . . . Mn can include any one of the following: —OH, —CONHR, —CONHCOR, —NHR, —COOH, —COOR, —CSNHR, —COR, —RCSR, —RSR, —ROR, —SOOR, —RSOR, —CONR$_2$, —(OCH$_2$CH$_2$)$_n$OH, —(OCH$_2$CH$_2$)$_n$OR—CH$_3$, —NR$_2$, —CN, —(CF$_2$)$_n$CF$_3$, —CO$_2$CH$_3$, —CONHCH$_3$, —CR, CHCH$_2$, —OCH$_2$CF$_2$CF$_3$, Cl, Br, olefins, and the like, and any combination thereof .

In the above list, R is hydrogen or an organic group such as a hydrocarbon or fluorinated hydrocarbon. As used herein, the term "hydrocarbon" includes alkyl, alkenyl, alkynyl, cycloalkyl, aryl, alkaryl, aralkyl, and the like. The hydrocarbon group may, for example, comprise methyl, propenyl, ethynyl, cyclohexyl, phenyl, tolyl, and benzyl groups. The term "fluorinated hydrocarbon" is meant to refer to fluorinated derivatives of the above-described hydrocarbon groups.

In another embodiment, J is a hydrocarbon chain with the formula —$(CH_2)_n$— where n is between 1 and 22, preferably between 2 and 18, more preferably between 2 and 12.

Other embodiments of the invention are 1) a surface that is a surface energy gradient, 2) a surface utilizing a surface energy gradient, 3) a surface that is a surface energy gradient as produced by any of the methods of the claims, and 4) a surface utilizing a surface energy gradient as produced by any of the methods of the claims.

Another embodiment of the invention is a surface as produced by any of the methods of the claims that is used in lab-on-a-chip technology.

In another embodiment, the monolayer surfaces of channels and passages are constructed and arranged such that a single drop or multiple drops of fluid requires less external force to move through channels and passages with the monolayer surface than channels and passages without the monolayer surface.

In another embodiment, the monolayer surfaces are constructed and arranged such that instead of having separate wells where the fluid is delivered and analyzed, the analysis could be done while the fluid moves along the channels. Reactive chemicals can be incorporated into the surface with the surface energy gradient so that the certain chemicals, proteins, etc. could be detected in the drop as it moves along the surface.

In another embodiment, the gradient is created on a standard micromachined array of channels in silicon. Because silicon oxide is a high-energy surface, water will wet it very easily, and friction losses would be high. The high-energy silicon oxide surface can be converted into a low-energy surface by depositing a SAM film on the silicon that will repel water and reduce friction. Based on the details of the experiments discussed in the previous section, one preferred SAM would be obtained from an alkylsilane-based surfactant with a silane head group X and a methyl (—$CH_3$) tail group M. The silane head group will bond with the silicon, resulting in a SAM film with a —$CH_3$ surface. The carbon chain backbone of the SAM should be a single chain and contain at least 12 carbons. This type of SAM will pack very closely, resulting in a lowered friction loss. A molecule with a carbon chain backbone of at least 6 carbons will still pack tightly as well.

In addition to reducing friction, another use for SAMs is in the area of fluid transport. An embodiment of the invention includes a design which gives a means of transporting liquids across a surface without using any external forces in some instances and reduced external forces in other cases. This self-propulsion of liquid drops allows microfabricated systems to be much more efficient.

An embodiment of the inventive method takes advantages of the ability of SAM films to modify the surface energy of a substrate. By changing the tail group of a SAM from, for example, a —$CH_3$ group to an —OH or —$CO_2H$ group, the surface can change from a low-energy surface to a high-energy surface. Water will not wet a low-energy surface, but it will wet a high-energy surface. Therefore, a surface having a surface energy gradient allows water to move across the surface from areas of low energy into areas of higher and higher surface energy. Embodiments of the SAMs of this invention can be used to create such a surface energy gradient.

In an embodiment of the inventive method, a mixed SAM surface is created on a silicon oxide semiconductor surface using two separate SAM surfactant solutions, an AFM tip for nanografting, and a flow controller with picoliter capability for liquid additions. The system is inventive and unique in that it creates a fluid-impervious surface with a gradient in surface energies.

Figure 2:
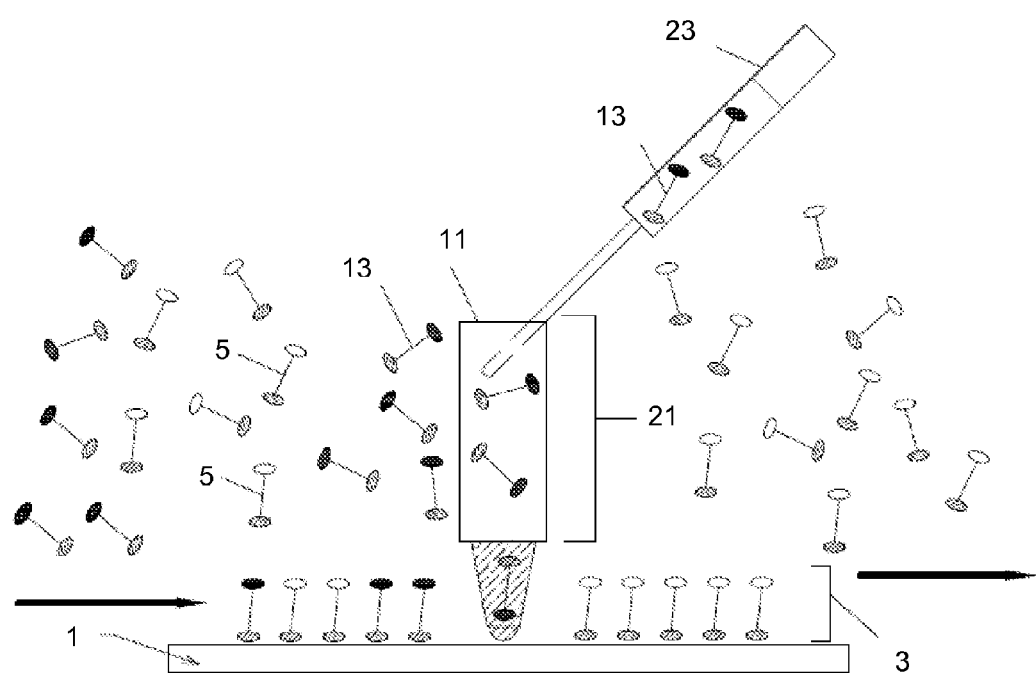
FIG. 2 illustrates a blown-up schematic view of the method during the removal and exposure steps wherein the instrument that removes the SAM layer also delivers new molecules to the surface.

In the first step of this embodiment, the semiconductor surface is exposed to a toluene solution containing an octadecyltrichlorosilane (this is the first SAM surfactant solution) capable of forming a SAM on the surface. FIG. 2 begins with the step at which this SAM surfactant solution has formed a SAM on the surface. In this example, five hours is sufficient to create a modified surface coated with a SAM film that has a methyl (—$CH_3$) tail group. This treatment creates a low-energy surface that repels water. In this embodiment, good results are obtained when the process is performed under an inert atmosphere such as nitrogen although it can be carried out under normal atmospheric conditions also.

In a specific embodiment, the surface being treated will remain in solution while an AFM tip passes over the surface and begins to remove parts of the original SAM and expose the original semiconductor surface. At the same time the AFM begins to remove the original SAM film, drops of toluene solution containing an organotrichlorosilane surfactant with a high-energy tail group such as —$CO_2H$ will be added to the solution The two surfactants (one with the high energy tail group the other with the low energy tail group) will form a mixed SAM on the area where the instrument scraped the previous SAM away. The instrument will continue to move along the original surface and remove the original SAM while more of the $CO_2H$-terminated surfactant is added to the solution. This process can continue along the entire length of the channel; as the instrument passes along the surface, the concentration of $CO_2H$-terminated surfactant continually increases in the solution. As the percentage of $CO_2H$-terminated surfactant in solution continually increases, the percentage of $CO_2H$-groups continually increases in the mixed monolayer that forms along the path of the AFM tip. The mixed SAM that forms will have a continuously increasing —$CO_2H$ concentration at the surface. Therefore, the surface energy increases along the length of the channel.

For One Silicon Embodiment

Octadecyltrichlorosilane ($CH_3(CH_2)_{17}SiCl_3$) in toluene can be used as low-energy surfactant (X1-J1-M1) where M1=$CH_3$
J1=$(CH_2)_{17}$
X1=$SiCl_3$ To create the gradient, a molecule (X2-J2-M2) can be used with any higher-energy surface group for M2 ($CO_2H$, OH, etc. or other moiety that has a higher surface energy than $CH_3$). For example, even =$CH_2$ has a higher energy than —$CH_3$. X2 and J2 can be the same as X1 and J1 in this embodiment.

For a Gold, Silver, or Copper Embodiment

Dodecanethiol ($CH_3(CH_2)_{11}SH$) in ethanol used as low-energy surfactant (X1-J1-M1) where

M1=$CH_3$
J1=$(CH_2)_{11}$
X1=SH

To create the gradient, another thiol of undecanoic acid ($CO_2H(CH_2)_{10}SH$) as high-energy surfactant (X2-J2-M2) can be used where

M2=$CO_2H$
J2=$(CH_2)_{10}$
X2=SH

Additional materials and functional groups suitable for use in the present invention can be found in U.S. Pat. No. 5,079,600, issued Jan. 7, 1992, and incorporated herein by reference.

The SAM-forming compound may terminate in a second end, opposite to the end bearing the functional group selected to bind to the surface material, with any of a variety of functionalities. That is, the compound may include a functionality that, when the compound forms a SAM on the surface material, is exposed. Such a functionality may be selected to create a SAM that is hydrophobic, hydrophilic, that selectively binds various biological or other chemical species, or the like. Other groups for M are found in columns 8 and 9 of U.S. Pat. No. 5,776,748.

U.S. Pat. No. 4,690,715 contains good examples of chemicals to use with different surfaces. Other useful patents are U.S. Pat. Nos. 5,620,850, 5,079,600, 5,512,131, 6,235,340. All of the above patents are herein incorporated by reference.

Another embodiment of an inventive method starts with a silicon or plastic surface that has a gold, silver, or copper coating on it. With this system embodiment, thiols could be used instead of silanes and ethanol could be used instead of toluene. The process could then take place under ambient conditions. Thiols offer more stability than silanes under many conditions, and ethanol is less hazardous than toluene. Also, the time required to form SAM films on gold, silver, and copper from thiols in solution is often much shorter than the time required to form SAMs from silanes. It can take as little as five minutes to form SAM films on gold surfaces using ethanol solutions containing thiols. It should be noted, that other SAM-forming compounds that work similarly to thiols or those having at least one sulfur-containing functional groups (e.g. sulfide or disulfide) can be selected.

Occasionally, trichlorosilanes or thiols with high-energy tail groups are difficult to synthesize. This method can still be used to create a surface energy gradient by using a trichlorosilane or thiols containing a tail group that has only a slightly higher surface energy than the tail group used in the first step.

The mixed-monolayer film that is formed can be reacted with other reagents to increase the surface energy gradient. For example, a trichlorosilane or thiols with a $=CH_2$ tail group could be used as the second surfactant M2 in this example. The resulting surface of $—CH_3$ and $=CH_2$ tail groups could undergo a series of reactions to convert the $=CH_2$ tail groups into $—CO_2H$ groups while leaving the $—CH_3$ groups unreacted. Thus, this process embodiment allows the surface energy gradient to be increased further.

In this embodiment of the invention, the resulting surface could allow for self-propulsion of water or other aqueous fluid or drops thereof. Such a drop of water or other aqueous fluid forms a decreasing contact angle along such a surface and has increasing forces of attraction to such a surface along its length. An organic or oil-bearing fluid could be propelled in a similar manner by starting with a high-energy surface (such as $—CO_2H$) and decreasing the surface energy along the length of the surface or channel using low-energy groups (such as $—CH_3$).

In an embodiment using water, if a drop of water is placed at the beginning of the channel, it will not wet the channel because of the low-energy methyl surface. However, it is attracted to the slightly higher energy surface composed of a mixed methyl and $—CO_2H$ surface. As the $CO_2H$ concentration of the surface increases, the force of attraction between the water and the surface increases. The contact angle between the advancing drop and the mixed-SAM surface decreases along the length of the channel. Therefore, the drop can propel itself across the surface without the use of any external forces. By changing the surfactant additions so that a surface is created with a surface energy gradient from high-surface energy to low-surface energy, the design would allow for a low-energy nonpolar molecule such as a drop of oil to propel itself across the surface. The design could also be used for systems where one merely wishes to reduce the external energy required to transfer a liquid across a surface.

It should be recognized to one skilled in the art that a multitude of surfaces and surfactants could be used in combinations to form monolayer films. Such combinations are considered covered by this invention. It should also be recognized to those skilled in the art that many different instruments capable of operating at the nanoscale-scale and smaller level can be used with this invention. Such uses are also covered by this invention. Means of optimizing this process by adjusting surfactant concentrations in solution, solutions used, exposure times, instrument speeds, geometries, temperatures, substrates, etc. to fit other systems are covered by this invention.

It should be noted that in another embodiment of the invention, the instrument that removes the original SAM film can also be used to deliver the mixed-SAM solution to the bare surface. For example, a reservoir inside the instrument could contain a mixed-SAM solution. This solution could then be delivered to the surface at an increasing rate of delivery so that the surface energy gradient is created.

In another embodiment, the mixing of the SAM solutions could take place inside the reservoir. The composition of the mixed-SAM solution would change as one SAM solution is gradually added to the original solution inside the reservoir. This solution could then be delivered to the surface at a constant rate of delivery so that the surface energy gradient is created.

In another embodiment, the mixing could take place outside the reservoir and then delivered to the surface by various means, one embodiment of which is through the removal instrument.

In another embodiment, it is not necessary for the reservoir in either example to contain a mixed-SAM solution. It can contain only one SAM in solution. The rate of delivery of this solution could be varied to create the surface energy gradient.

In another embodiment, the surface is used for improving fluid flow in diagnostic systems that incorporate chemical, biological, or genomic sensors on the surface. It is also useful in making such systems even smaller and more efficient.

In some preferred embodiments, at least one of the molecules of formula (X-J-M) chosen to form the monolayers is resistant to the adsorption of biopolymers such as proteins, enzymes, antibodies, polynucleic acids, cells, and other biological molecules. By the term "resistant to the adsorption of biopolymers" it is meant that the base surface covered by the monolayer has a reduction in the amount of a biopolymer adsorbed on the surface, when contacted with a medium containing biopolymers available for adsorption, as compared to the amount adsorbed on the same base surface that is not covered by the monolayer.

For these embodiments, the J group of the molecule is a spacer moiety comprising a biopolymer-resistant domain. Suitable moieties for the biopolymer-resistant domain of the J group are discussed in U.S. Pat. No. 6,235,340 and include oligoethers, oligo glycols, oligoalcohols, oligo carbonyls, oligo sulfides, oligosulfones and oligosaccharides. Such moieties typically are used to produce a monolayer that is both hydrophilic and biopolymer-resistant.

In one embodiment, the biopolymer-resistant domain comprises an oligo-(ethylene glycol) linkage ($—OCH_2CH_2—$)$_n$ where n is 2 to 4.

For embodiments with monolayers (either mixed or uniform) comprising biopolymer resistant molecules, the surface to be treated may be a blood-contacting surface, or it may be some other type of surface, e.g. the surface of a biosensor, bioseparation chamber, or the surface of an electronic device or component or of an electrochemical detection or analysis device. It may be a surface of a finished device such as a blood-contacting device or it may be the surface of a material to be used in forming a finished device. In the latter case subsequent forming steps are selected to avoid disrupting the coating formed by the process of the invention in portions of the device where the coating will protect the surface in use and to avoid chemical damage, for instance due to high temperatures, to the coating. Such coated surfaces therefore have applications in blood contacting devices and in devices where reduced non-specific protein adsorption is desirable, for instance in diagnostic devices which require a specific interaction of an analyte and detector species, e.g. biosensors, bioseparation membranes and sight correction devices.

In one embodiment, the invention can be used for improving medical or laboratory devices to increase biocompatibility and resistance to protein binding.

In another embodiment, the surface gradient is created on DNA microarray slides. Current slides are composed of single strands of DNA attached on a glass slide to form discrete dots in an array pattern. Several hundred or more dots currently can be put on a slide. A solution containing single strands of DNA is poured on top of the slide. The DNA strands in solution eventually match up to the matching stationary strand on the slide. Because the slides are manufactured so that the specific location and composition of the stationary strand is known, one can determine the DNA make-up of the solution by identifying where the DNA coupling reaction occurs.

A further embodiment of this invention, would improve the fluid transport across the slide. Instead of waiting for the DNA strands to diffuse through solution until it finds its matching strand, the fluid is directed across the slide so that it is distributed more efficiently. This would also make the slides much smaller. Rather than having strands in dots, they could be in a series of lines along the surface. As the fluid moves across the surface due to the surface energy gradient, the DNA will react to the matching strand as it passes over it.

Another embodiment is the use of this surface in miniaturized systems that require cooling. The fluid is transported through coolant channels using the surface energy gradient. Reducing the surface tension of a fluid allows it to flow into regions of smaller and smaller dimensions. Any type of semiconductor, electromechanical, or optoelectronic device that requires cooling to operate the most efficiently could use this technology. The invention would also allow such systems to be made even smaller because the size of the device would not face the heat transfer limitations that many current devices have.

Another embodiment is the use of the surface gradient in medical devices, treatments and artificial organs. Small tubes with a surface energy gradient on the inside surface are able to function as capillaries or other blood vessels. The blood would naturally flow through the tube; surface tension would not prevent it from moving into recesses and other extremely small openings.

Another embodiment is the use of the surface gradient in depositing metal or other components on hard to reach and surfaces in corners or deep recesses. For example, an electroless plating solution could be transported to an inside corner deep within an object using this invention. Metal could then be deposited in an area that was previously unable to be coated.

Another embodiment is the use of the surface gradient in not only just using these systems to merely detect and analyze solutions, this invention can be used in objects and devices that actually treat and/or deliver medical benefits. For instance, a vein or artery surface (either natural or artificial) could be treated so that it has a surface energy gradient that causes plaque or cholesterol particles to be transported to specific areas where they are reacted with a component that destroys them in solution. This would prevent cholesterol from building up on the walls.

Another embodiment is the use of the surface gradient in integration with biopharmaceutical molecules that recognize a certain genetic or protein sequence. When virus or cancer or other disease molecules containing that sequence are transported across the surface, the reactive chemical recognizes the sequence of interest and kills the harmful molecule.

FIG. 2 shows a blown-up schematic view of the method during the removal and exposure steps wherein the instrument 11 that removes the SAM layer 3 also delivers new molecules 13 to the base surface 1. In this manner the mixing of first molecules 5 and second molecules 13 is performed near the base surface 1 as the instrument 11 delivers second molecules 13 from the instrument reservoir 21. The instrument 11 can have the new molecules 13 stored in the instrument reservoir 21 inside the instrument 11 or added to the instrument 11 by tool 23 as the instrument 11 passes along the surface 1.

Figure 3:
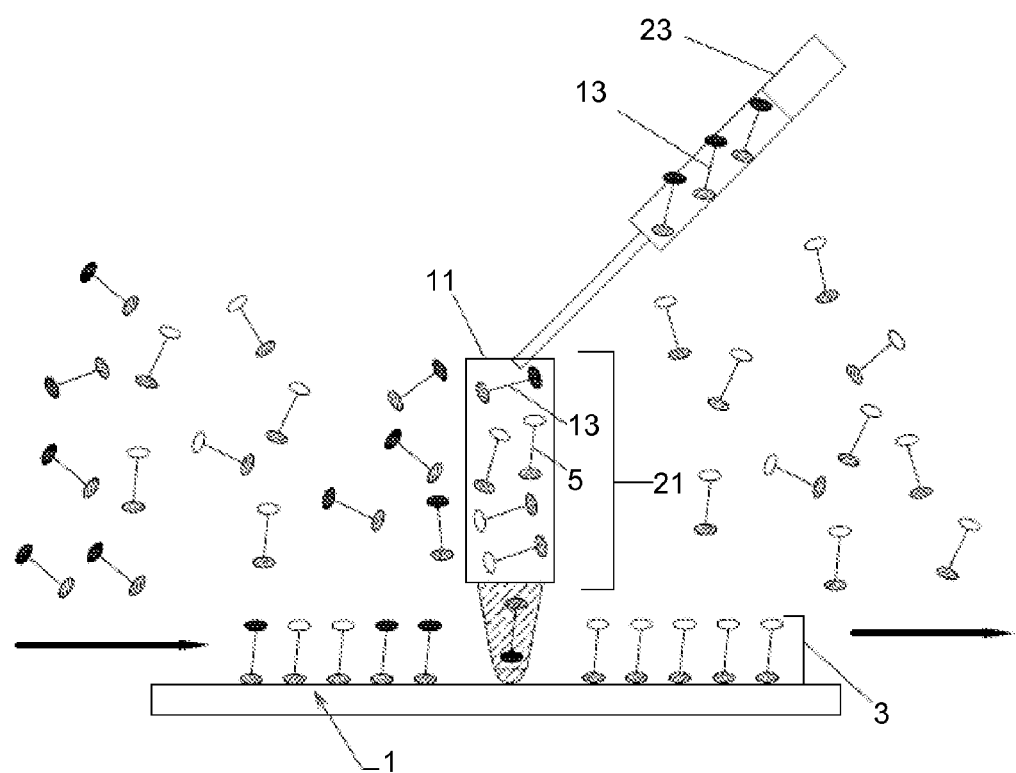
FIG. 3 illustrates a blown-up schematic view of the method during the removal and exposure steps wherein the instrument that removes the SAM layer also delivers mixture to the surface.

FIG. 3 shows a blown-up schematic view of the method during the removal and exposure steps wherein the instrument 11 that removes the SAM layer 3 also delivers new molecules 13 to the base surface 1. In this manner the mixing of first molecules 5 and second molecules 13 is performed inside the instrument reservoir 21 and then the mixture is delivered near the base surface 1 as the instrument 11 delivers second molecules 13 from the instrument reservoir 21. The instrument 11 can have the new molecules 13 stored in the instrument reservoir 21 inside the instrument 11 or added to the instrument 11 by tool 23 as the instrument 11 passes along the surface 1.

Figure 4:
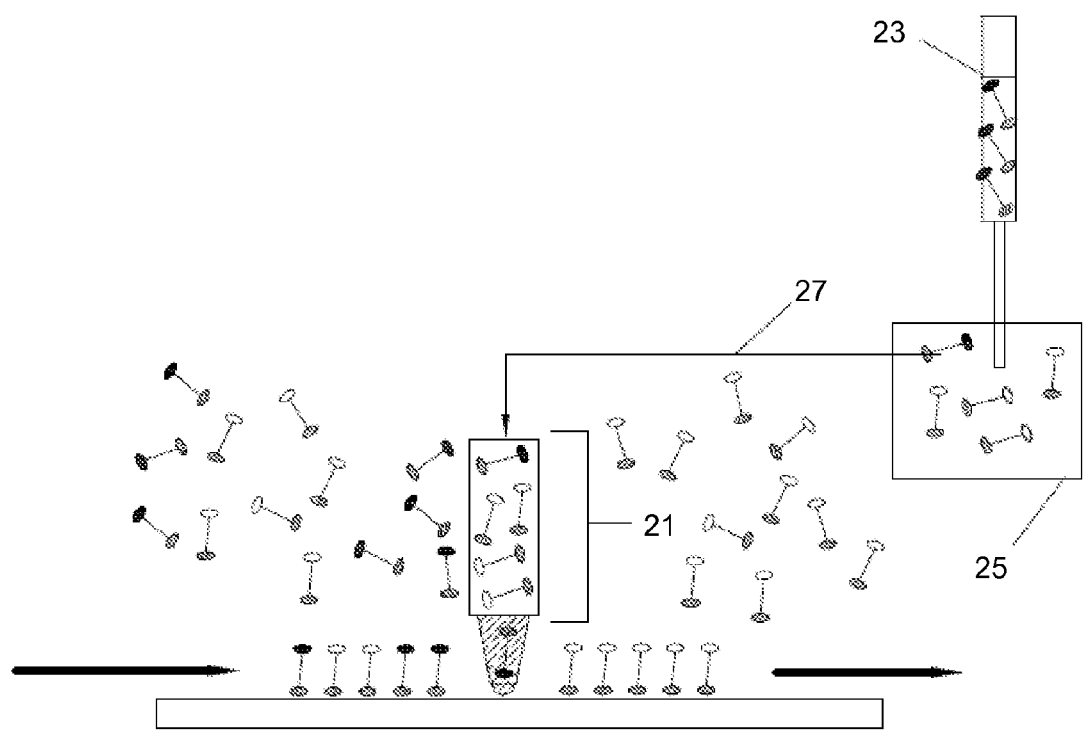
FIG. 4 illustrates a blown-up schematic view of the method during the removal and exposure steps wherein the instrument that removes the SAM layer also delivers new molecules to the surface which are mixed in an outside reservoir.

FIG. 4 illustrates another method of mixing. Here, the mixing method has similarities to those illustrated in FIG. 2 and FIG. 3, However the mixing of molecules is performed in an outside reservoir 25. The mixed molecules are then transferred into the instrument reservoir 21 by means of a line 27.

Figure 5:
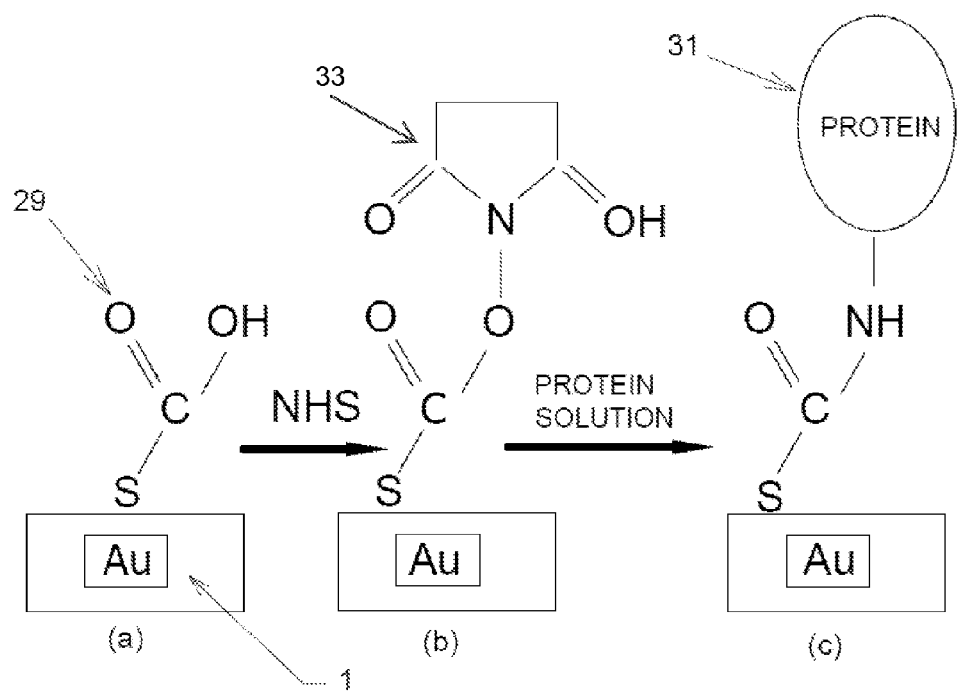
FIG. 5 illustrates a schematic view of the end condition for a representative method for reacting a mixed monolayer to incorporate a gradient of other chemical species. In this figure the portions of the $CH_3$—$CO_2H$ mixed monolayer that do not take part in the reaction are not shown (e.g. $CH_3$).

In FIG. 5, the mixed-SAM surface 29 reacts with NHS (N-hydroxy succinimide) to produce a surface with an increasing concentration of NHS ester (step b). It should be noted that the portions of the $CH_3$—$CO_2H$ mixed monolayer that do not take part in the reaction are not shown (e.g. $CH_3$). Various proteins 31 containing lysine groups can then be adsorbed by NHS-surfaces 33 (step c). The NHS-surface 33 functions to self-propel or reduce the external force requirements necessary for propulsion of a liquid (e.g. blood) while removing protein molecules from the liquid. Similar designs could have a wide application in analyzing blood, other protein-bearing liquids, and liquids containing oligo-strands of DNA, as well as antigen/antibody combinations. This NHS-surface and other such surfaces use SAM surfaces such as these, with properties tailored to adsorb specific molecules, and provides means to effectively decrease the necessary dimensions of such analytical systems. This system could also be applied to stent technology so as to remove harmful proteins or fats from collecting in arteries and other such body lumens.

Figure 6:
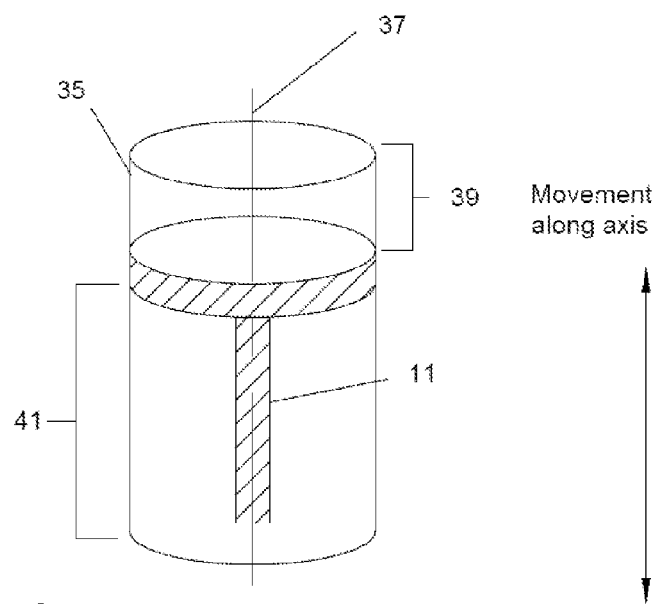
FIG. 6 illustrates a side elevational view of a method for creating a gradient along the walls of the tube in a direction along a longitudinal axis through the center of the tube.

FIG. 6 illustrates a method for creating a surface energy gradient on the inside of a tube 35. In this instance, the instrument 11 is in contact with the uniform surface energy monolayer on the inside walls of the tube 35 and moves along the inside of the tube 35 in a direction longitudinal to the longitudinal axis 37 removing the uniform surface energy monolayer. The second organic molecules having a different functional group than that of the removed monolayer can be in solution above the instrument in upper area 39, below in lower area 41, or in both upper area 39 or lower area 41. The solution can also flow through a hollow cavity in the instrument 11 so as to reach the surface to be treated. As more second organic molecules are added a greater number will react with the portion of the tube which has had the uniform surface energy monolayer removed. In this way a longitudinal gradient is created on the inside walls of the tube 35.

Figure 7:
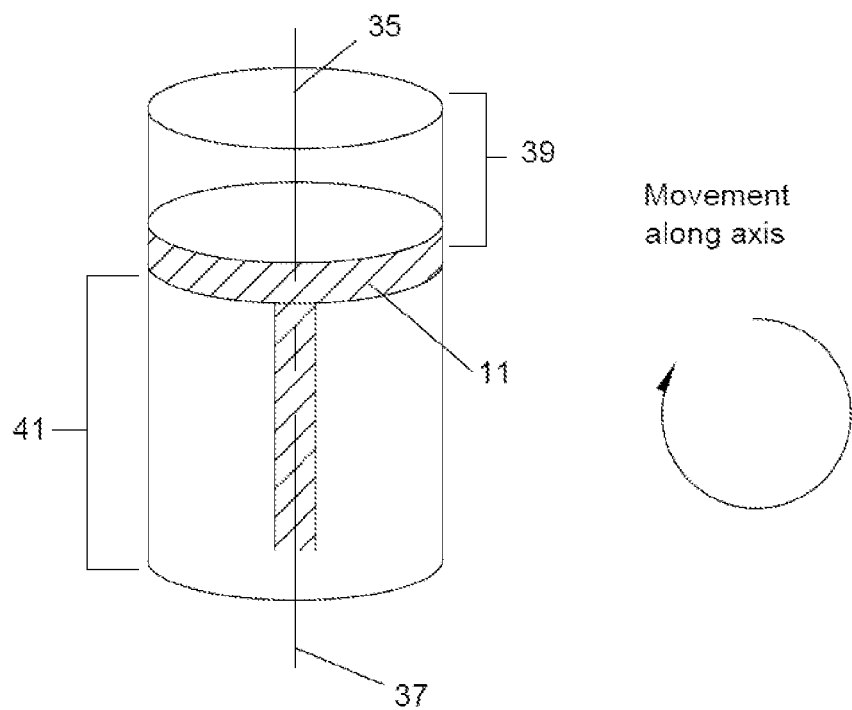
FIG. 7 illustrates a side elevational view of a method for creating a gradient on the walls of the tube in a strip formed by rotating the instrument about the longitudinal axis through the center of the tube.

FIG. 7 illustrates a similar method for creating a surface energy gradient on the inside of a tube 35. However, in this instance, the instrument 11 is in contact with the uniform surface energy monolayer on the inside walls of the tube 35 and moves along the inside of the tube 35 in a rotational direction about the longitudinal axis 37 removing the uniform surface energy monolayer. The second organic molecules having a different functional group than that of the removed monolayer can be in solution above the instrument in upper area 39, below in lower area 41, or in both upper area 39 and lower area 41. The solution can also flow through a hollow cavity in the instrument 11 so as to reach the surface to be treated. As more second organic molecules are added a greater number will react with the portion of the tube which has had thee uniform surface energy monolayer removed. In this way a gradient is created on the inside walls of the tube 35 about a strip on the radius.

Figure 8:
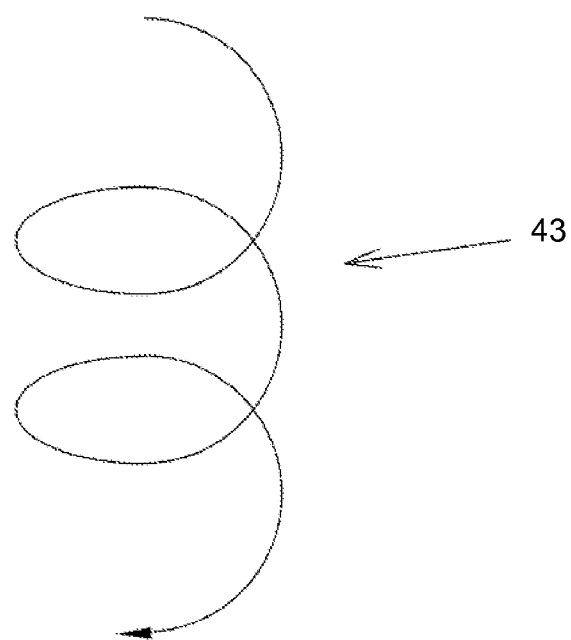
FIG. 8 illustrates a schematic view of a spiral surface energy gradient that might be produced on the inside of a tube when the movements of FIG. 6 and FIG. 7 are combined.

FIG. 8 illustrates a schematic of the pattern of surface energy gradient 43 created if the instrument 11 from FIG. 7 is in contact with the uniform surface energy monolayer on the inside walls of the tube 35 and moves along the inside of the tube 35 in a rotational direction about the longitudinal axis 37 and in a longitudinal direction along the longitudinal axis 37 removing the uniform surface energy monolayer. The second organic molecules having a different functional group than that of the removed monolayer can be in solution above the instrument in upper area 39, below in lower area 41, or in both upper area 39 or lower area 41. The solution can also flow through a hollow cavity in the instrument 11 so as to reach the surface to be treated As more second organic molecules are added a greater number will react with the portion of the tube which has had the uniform surface energy monolayer removed. In this way a gradient is created on the inside walls of the tube 35 in a spiral type pattern.

FIG. 9 illustrates a method for creating a surface energy gradient on the outside side of a tube 35. In this instance, the instrument 11 is in contact with the uniform surface energy monolayer on the outside walls of the tube 35 and moves along the outside of the tube 35 in a direction longitudinal to the longitudinal axis 37 removing the uniform surface energy monolayer. The direction of the instrument's movement can also be rotational about the longitudinal axis 37 or a combination of rotational and longitudinal movement thereby creating a spiral gradient on the outside of the tube. The second organic molecules having a different functional group than that of the removed monolayer can be in solution above the longitudinal instrument contact point 45 in upper area 39, below in lower area 41, or in both upper area 39 or lower area 41. The solution can also flow through a hollow cavity in the instrument 11 so as to reach the surface to be treated. As more second organic molecules are added a greater number will react with the portion of the tube which has had the uniform surface energy monolayer removed. In this way a gradient is created on the outside walls of the tube 35.

FIGS. 10 and 11 illustrate how the surface energy gradient can be created on only specific portions of the tube. By employing the same methods and mechanisms as those of FIGS. 6, 7, 8, and 9 with the addition of teeth or tips 47 even more specific portions of surface energy gradient can be created on the inside of the tube 35 as in FIG. 10 and the outside of the tube as in FIG. 11.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

Such information as may be found relating to portions of this application include:

Kataoka, Dawn E. and Troian, Sandra M., "Patterning Liquid Flow on the Microscopic Scale," Nature, Vol. 402, December 1999, pp. 794-797.

Kim, H., Graupe, M., Oloba, O., Koini, T., Imaduddin, S., Lee, T., and Perry, S., "Molecularly Specific Studies of the Frictional Properties of Monolayer Films: A Systematic Comparison of CF3-, (CH3)2CH—, and CH3-Terminated Films," Langmuir, 1999, Vol. 15, pp. 3179-3185.

Krim, J. "Atomic-Scale Origins of Friction," Langmuir, 1996, Vol. 12, pp. 4564-4566.

Laibinis, P., Palmer, B., Lee, S., and Jennings, G. K., "The Synthesis of Organothiols and Their Assembly into Monolayers on Gold, " Thin Films Vol. 24, 1998.

Laibinis, P., Fox, M., Folkers, J., and Whitesides, G., "Comparisons of Self-Assembled Monolayers on Silver and Gold," Langmuir, 1991, Vol. 7, pp. 3167-3173.

Lee, S., Shon, Y., Colorado, R., Guenard, R., Lee, T., and Perry, S., "The Influence of Packing Densities and Surface Order on the Frictional Properties of Alkanethiol Self-Assembled Monolayers (SAMs) on Gold, Langmuir, 2000, Vol. 16, pp. 2220-2224.

Liu, Y. and Evans, D., "Structure and Frictional Properties of Self-assembled Surfactant Monolayers," Langmuir, 1996, Vol. 12, pp. 1235-1244.

Patel, N., Davies, M., Hartshorne, M., Heaton, R., Roberts, C., Tendler, S., and Williams, P., "Immobilization of Protein Molecules onto Homogenous and Mixed Carboxylate-Terminated Self-Assembled Monolayers," Langmuir, 1997, Vol. 13, pp. 6485-6490.

Pfahler, J, Harley, J., and Bau, H., "Liquid Transport in Micron and Submicron Channels," Sensors and Actuators, A21-23, 1990, pp. 431-434.

Tsukruk, V., and Bliznyuk, V., "Adhesive and Friction Forces Between Chemically Modified Silicon and Silicon Nitride Surfaces, " Langmuir, 1998, Vol. 14, pp. 446-455.

Xiao, X., Hu, J., Charych, D., and Salmeron, M., "Chain Length Dependence of the Frictional Properties of Alkylsilane Molecules Self-Assembled on Mica Studied by Atomic Force Microscopy," Langmuir, 1996, Vol. 12, pp. 235-237.

Xu, S., Miller, S., Laibinis, P, and Liu, G., "Fabrication of Nanometer Scale Patterns within Self-Assembled Monolayers by Nanografting," Langmuir, 1999, Vol. 15, pp. 7244-7251.

U.S. Pat. No. 6,235,340
U.S. Pat. No. 5,512,131
U.S. Pat. No. 5,776,748
U.S. Pat. No. 4,690,715
U.S. Pat. No. 5,620,850
U.S. Pat. No. 5,079,600

All US patents and applications and all other published documents mentioned anywhere in this application are incorporated herein by reference in their entirety.

I claim:

1. A medical device comprising at least one distinct region of length L and width W of the surface of the device covered by a mixed monolayer film, the mixed monolayer film comprising a species having a functional group M1 and a species having a functional group M2 where M1 and M2 have different surface eneries, the mixed monolayer forming a surface energy gradient from proximal location to a distal location within the region wherein L equals the distance from the proximal location to the distal location, W is 20 nanometers or greater, and the ratio of L/W is greater than 2 and wherein at least one of the species comprises a biopolymer-resistant domain and wherein any portions of the surface that border the at least one distinct region along the dimension L have substantially equal surface energies.

2. The device of claim 1 wherein any portions of the surface that border the at least one distinct region along the dimension L are covered by substantially uniform monolayers.

3. The device of claim 2 wherein the substantially uniform monolayers comprise biopolymer-resistant domains.

4. The device of claim 1 wherein the biopolymer-resistant domain comprises an oligo-(ethylene glycol) linkage.

5. The device of claim 3 wherein the biopolymer-resistant domain comprises an oligo-(ethylene glycol) linkage.

6. The device of claim 1 where the ratio of L/W is greater than 10.

7. An analytical device comprising a fluid-impervious surface comprising a base surface, at least one distinct region of length L and width W of the base surface covered b a mixed monolayer film, the mixed monolayer film comprising a species having a functional group M1 and a species having a functional group M2 where M1 and M2 have different surface energies, the mixed monolayer forming a surface energy gradient from a proximal location to a distal location within the region wherein L equals the distance from the proximal location to the distal location W is 20 nanometers or greater, and the ratio of L/W is greater than 2 and wherein any portions of the surface that border the at least one distinct region along the dimension L have substantially equal surface energies and wherein at least one of the species comprises a biopolymer-resistant domain and wherein at least one of the regions comprising the surface energy gradient is defined in a series of channels and passages.

8. The device of claim 7, wherein the surface gradient of channels and passages are constructed and arranged such that fluid requires less external energy to move through channels and passages with the surface gradient than channels and passages without the surface gradient.

9. The device of claim 7, wherein the surface gradients are constructed and arranged to deliver fluid to separate wells for analysis.

10. The device of claim 7, wherein the surface gradients comprise reactive chemicals for detecting the presence of chemical species, proteins, and the like as the fluid moves along the surface.

11. The device of claim 7 wherein any portions of the surface that border the at least one distinct region along the dimension L are covered by substantially uniform monolayers.

12. The device of claim 11 wherein the substantially uniform monolayers comprise biopolymer-resistant domains.

13. The device of claim 12 wherein the biopolymer-resistant domain comprises an oligo-(ethylene glycol) linkage.

14. The device of claim 7 wherein the biopolymer-resistant domain comprises an oligo-(ethylene glycol) linkage.

15. The device of claim 1, wherein the mixed monolayer is formed from species X1-J1-M1 and X2-J2-M2 wherein X1, X2, M1, and M2 represent separate functional groups where M1 and M2 have different surface energies and J1 and J2 represents spacer moieties, the species X1-J1-M1 and X2-J2-M2 forming a self-assembled monolayer onto the base surface from solution.

16. The device of claim 1 wherein the molar concentration of the species comprising the functional group M2 continuously increases relative to the concentration of the species comprising functional group M1 from the proximal location to the distal location of the region having the mixed monolayer.

17. The device of claim 7, wherein the mixed monolayer is formed from species X1-J1-M1 and X2-J2-M2 wherein X1, X2, M1, and M2 represent separate functional groups where M1 and M2 have different surface energies and J1 and J2 represents spacer moieties, the species X1-J1-M1 and X2-J2-M2 forming a self-assembled monolayer onto the base surface from solution.

18. The device of claim 7 wherein the molar concentration of the species comprising the functional group M2 continuously increases relative to the concentration of the species comprising functional group M1 from the proximal location to the distal location of the region having the mixed monolayer.

* * * * *